United States Patent

Ashby et al.

[11] Patent Number: 5,989,472
[45] Date of Patent: Nov. 23, 1999

[54] METHOD FOR MAKING A REINFORCED ORTHOPEDIC IMPLANT

[75] Inventors: Alan M. Ashby, Weygand, France; Declan P. Slemon, Limerick, Ireland; Melvin Schwartz, Jr., Point Pleasant, N.J.

[73] Assignee: Howmedica International, Inc., Ireland

[21] Appl. No.: 08/915,246

[22] Filed: Aug. 20, 1997

Related U.S. Application Data

[63] Continuation of application No. 08/536,286, Sep. 29, 1995, abandoned.

[30] Foreign Application Priority Data

Oct. 5, 1994 [GB] United Kingdom .................... 9420071

[51] Int. Cl.⁶ .................................................. B29C 69/00
[52] U.S. Cl. ........................... 264/273; 264/250; 264/274; 623/18
[58] Field of Search ..................................... 264/273, 274, 264/250; 623/20, 18

[56] References Cited

U.S. PATENT DOCUMENTS

| | | | |
|---|---|---|---|
| 1,606,680 | 11/1926 | Wisner | 264/274 X |
| 4,479,271 | 10/1984 | Bolesky et al. | 623/20 |
| 4,924,583 | 5/1990 | Hummel et al. | 264/273 X |
| 4,997,445 | 3/1991 | Hodorek | 623/16 |
| 5,019,104 | 5/1991 | Whiteside et al. | 264/274 X |
| 5,108,435 | 4/1992 | Gustavson | 623/16 |
| 5,181,924 | 1/1993 | Gschwend et al. | 623/20 |

FOREIGN PATENT DOCUMENTS

| | | |
|---|---|---|
| 0438918 | 7/1991 | European Pat. Off. . |
| 0522999 | 1/1993 | European Pat. Off. . |

*Primary Examiner*—Jan H. Silbaugh
*Assistant Examiner*—Mark Eashoo
*Attorney, Agent, or Firm*—Lerner, David, Littenberg, Krumholz & Mentlik, LLP

[57] ABSTRACT

A metal backing for inclusion in the manufacture of a prosthetic component having a plastic on an upper surface and has a bottom surface portion with elements for attachment to a bone. The backing has an upper surface portion at least part of which is formed by a grill element having exposed front and rear faces and which is intended to be embedded within the plastic bearing member during construction. The plastic bearing material of the bearing element can be molded so that all the faces thereof exposed to the grill are covered and the grill is embedded within the plastic material of the bearing element. The grill is located on a metal support and is provided with spacers on its front face to space the front face away from the support. The grill is cast integrally into the metal support during manufacture. The casting process includes casting a grill on both outer surfaces of the metal backing with the grill element including cross-members spaced from backing surfaces. The polymeric bearing surface is molded around a first of the grill elements with the mechanical interlock between the bearing and the backing being provided by the molding of the polymeric material underneath the grill cross-members.

1 Claim, 2 Drawing Sheets

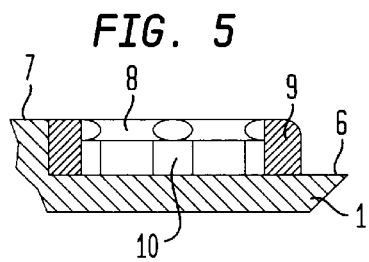
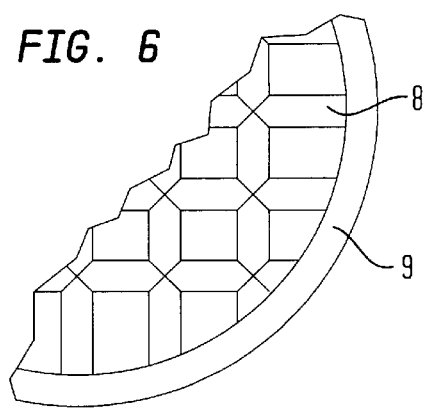
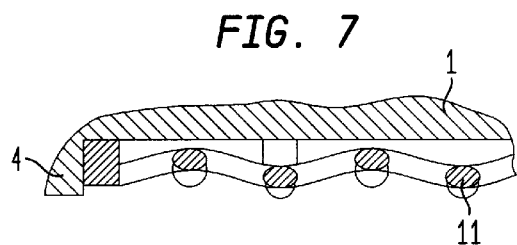
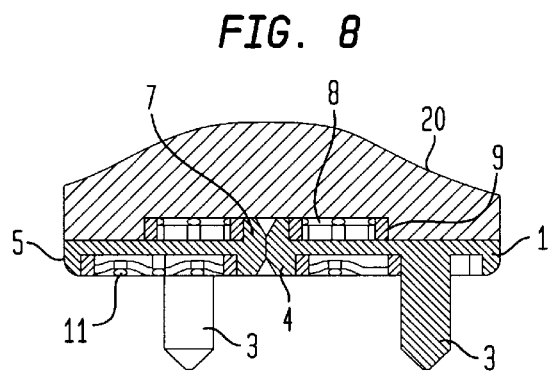
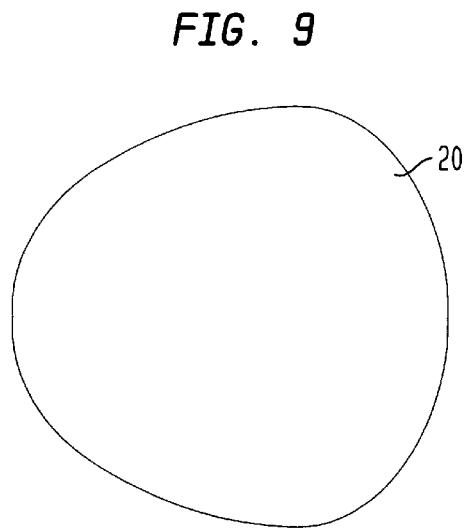

METHOD FOR MAKING A REINFORCED ORTHOPEDIC IMPLANT

This is a continuation of application Ser. No. 08/536,286, filed on Sep. 29, 1995, now abandoned.

BACKGROUND OF THE INVENTION

1. Field of the Invention

This invention relates to a metal backing for inclusion in the manufacture of a prosthetic component and to a metal component incorporating such a backing. More particularly it relates to a means of securing a synthetic plastic material such as polyethylene to a metal backing.

2. Description of the Prior Art

There are often difficulties in securing a metal backing to the synthetic plastic material of a bearing member, sometimes because of the limited space available.

Metal-backed patella components are well known within the industry. They have been subject to limitations on performance related to the small available space for their construction. Generally the factor affecting performance is the reliable and long term attachment of the plastic bearing elements to the metal backing which is used to provide the fixation surface of the device, either for cemented use or for biological ingrowth type applications. Traditional products have used riveting, snapping or molding techniques to provide for the interconnection of parts, these generally being geometric interference caused by this form of gross metal features on the metal backing, posts, holes, rims, etc.

U.S. Pat. No. 5,108,435 relates to an orthopedic implant having a cast mesh tissue ingrowth surface.

The present invention also has applications with regard to other metal backed components, for example, tibial components, elbow and shoulder components and hip cups.

SUMMARY OF THE INVENTION

According to the present invention a metal backing for inclusion in the manufacture of a prosthetic component which has a synthetic polymeric bearing element comprises a metallic element having a front portion with means for attachment to a bone and a rear portion at least part of which is formed by a grill having exposed front and rear faces and which is intended to be embedded within the bearing member during construction.

Thus, due to the construction of the metallic element, the synthetic plastic bearing material of the bearing element can be molded so that both exposed faces of the grill are covered and the grill is embedded within the synthetic plastics material bearing element.

Preferably the grill is located on a metal support and is provided with spacers on its front face to space said front face away from said support. The grill can be cast integrally into said metal support during manufacture.

In one preferred embodiment the front portion of the metal backing is provided with means for attachment to a bone with cement. In an alternative construction the metal backing can be provided with means for mechanical attachment to a bone. Thus, the front portion can be provided with a biological ingrowth surface to facilitate bone ingrowth.

With this arrangement the front portion of the metal backing can be provided with an intricate metal wire mesh and this mesh can be cast integrally into one side of a metal support on the other side of which said grill is located.

The invention also includes a prosthetic metal backed component including a metal backing set forth above and a synthetic plastics material bearing element having a rear bearing surface and a front portion within which the grill is embedded.

With this arrangement the grill is preferably molded integrally into the bearing element during manufacture. As mentioned above the invention is particularly, although not exclusively, applicable for use with a patella component.

The invention can be performed in various ways but one embodiment showing the application of the invention to a patella component will now be described by way of example and with reference to the accompanying drawings.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 5 is an enlarged cross-sectional view of a part of FIG. 2;

FIG. 6 is an enlarged part-plan view showing the grill;

FIG. 7 is an enlarged part-cross-sectional elevation of the underside of FIG. 2;

FIG. 8 is a cross-sectional side elevation of a complete prosthetic metal backed bearing component embodying the metal backing shown in FIGS. 1 to 7; and, FIG. 9 is a plan view of the component shown in FIG. 8.

DESCRIPTION OF THE PREFERRED EMBODIMENT

Figure 1:
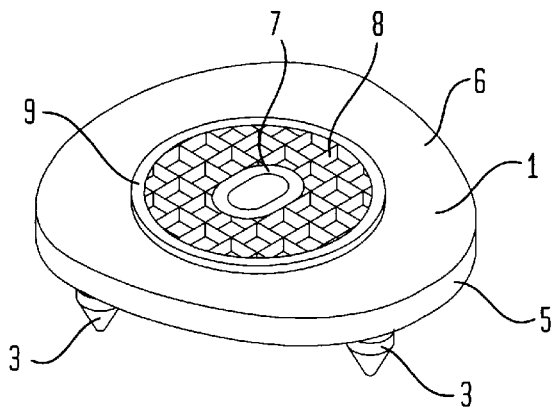
FIG. 1 is an isometric view of a metal backing for inclusion in the manufacture of a prosthetic patella component.
Figure 2:
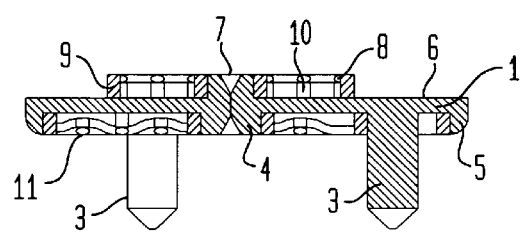
FIG. 2 is a cross-sectional side elevation through the component shown in FIG. 1.
Figure 3:
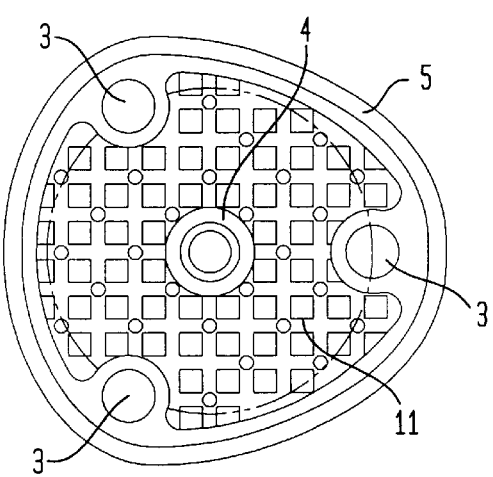
FIG. 3 is a plan view from beneath the component shown in FIGS. 1 and 2.
Figure 4:
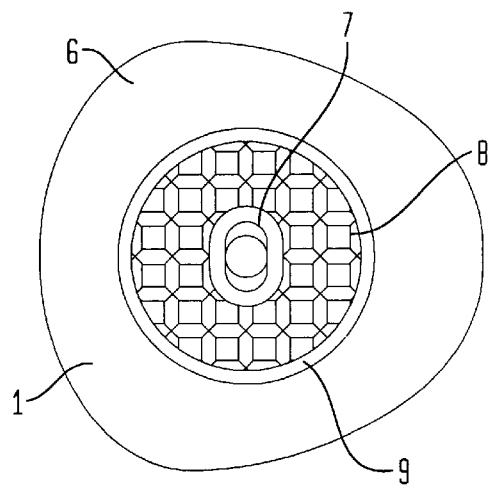
FIG. 4 is a plan view from above the same component.

FIGS. 1 to 7 show a metal backing for inclusion in the manufacture of a prosthetic patella component and comprises a shaped plate like metal support 1 on the front face of which is provided three location pins 3 and a central boss 4. On this face there is also a surrounding rim 5. The rear face 6 (top face of FIG. 2) is substantially flat apart from a projecting boss 7. Mounted on the boss 7 is a grill 8 having an outer rim 9. The grill is formed from substantially oval section members, best shown in FIG. 5, and is spaced away from the face 6 by integral supports (support posts) 10.

The space between the rim 5 on the front face and the boss is filled with a intricate metal mesh 11 as is most clearly shown in FIG. 7. The metal mesh 11 provides an ingrowth surface on the front face which is intended to be next to the prepared bone and the grill 8 is intended to be embedded in a synthetic plastic material bearing element to be described hereunder. The grill and wire mesh are preferably integrally cast with the metal support 1 using an investment casting technique where wax patterns for the castings are either assembled prior to casting, or ceramic inserts are used. Such a technique is taught in U.S. Pat. No. 5,108,435 the teachings of which are incorporated herein by reference.

The metal backing is used with a synthetic plastic material (such as ultra high molecular-weight polyethylene) bearing element 20 as shown in FIG. 8. In plan view the bearing element 20 is substantially the same shape as the support 1.

Subsequent to the casting and finishing of the metal component, this component is then used as an insert within a plastic compression mold and polymer powder, for example, ultra-high molecular weight polyethylene (UHMWPE) bearing material is loaded on top of the backing plate and compression molded in place to yield the construction shown in FIG. 8. During this process the plastic material under the pressure and heat of the molding operation forms a continuous structure underneath the grill 8 thereby providing an excellent mechanical lock between the two parts.

Due to this construction it is possible to reduce the thickness of the metal structure so that a larger thickness of bearing plastic can be formed above it. This is in part because of the efficiency of the mechanical interlocking system but also because the grill construction reinforces the metal substrate of the component. A biological fixation surface in the opposite side of the component may be formed by the same general process, or by other techniques well known in the industry.

In the arrangement described, the metallic mesh 11 is intended to provide ingrowth, but if desired any suitable other surface could be used or a cement fixation surface can be applied in any manner well known in the art.

As described above, the invention is applied to a metal backed patella component but it can be used in other metal backed components, for example, tibial components, elbow and shoulder components and hip cups where the ability to provide a rigid fixation in a restricted area will allow increased thickness of bearing material.

While several examples of the present invention have been described, it is obvious that many changes and modifications may be made thereunto, without departing from the spirit and scope of the invention.

We claim:

1. A process for manufacturing a reinforced orthopedic implant having a polymeric bearing surface thereon, comprising:

integrally casting, by investment casting, a metal backing for a orthopedic implant having a front face and a rear face, the front face of the metal backing being provided with location pins, a central boss, a surrounding rim and a metal mesh between the central boss and surrounding rim, wherein the metal mesh is spaced away from the front surface by support posts, the rear face of the metal backing having a projecting boss, an outer rim, and a metal grill between the projecting boss and outer rim, wherein the metal grill is spaced away from the rear surface by support posts, and molding a polymeric bearing material on the rear face of the metal backing thereby forming a continuous polymeric structure on the rear face of the metal backing and underneath the metal grill to embed the metal grill in the continuous polymeric structure, the continuous polymeric structure having the metal grill embedded therein includes the polymeric bearing surface having substantially the same shape as the metal backing.

* * * * *